(12) United States Patent
Hartwig et al.

(10) Patent No.: US 12,263,267 B2
(45) Date of Patent: Apr. 1, 2025

(54) LAMELLAR ARRANGEMENT AND DEVICE FOR STERILIZING A FLUID BY MEANS OF UV RADIATION COMPRISING SUCH A LAMELLAR ARRANGEMENT

(71) Applicant: OSRAM GMBH, Munich (DE)

(72) Inventors: Ulrich Hartwig, Berlin (DE); Markus Stange, Berlin (DE); Thorsten Klebba, Berlin (DE); Tobias Gleitsmann, Michendorf (DE); Mathias Bruemmer, Wusterwitz (DE); Rainer Quandt, Berlin (DE); Werner Stolzenberg, Berlin (DE)

(73) Assignee: OSRAM GMBH, Munich (DE)

( * ) Notice: Subject to any disclaimer, the term of this patent is extended or adjusted under 35 U.S.C. 154(b) by 304 days.

(21) Appl. No.: 17/934,966

(22) Filed: Sep. 23, 2022

(65) Prior Publication Data

US 2023/0097822 A1    Mar. 30, 2023

(30) Foreign Application Priority Data

Sep. 24, 2021    (DE) ..................... 10 2021 210 688.9

(51) Int. Cl.
  *A61L 2/26*    (2006.01)
  *A61L 2/10*    (2006.01)
  *A61L 9/20*    (2006.01)
(52) U.S. Cl.
  CPC    *A61L 2/26* (2013.01); *A61L 2/10* (2013.01); *A61L 9/20* (2013.01)

(58) Field of Classification Search
  None
  See application file for complete search history.

(56) References Cited

U.S. PATENT DOCUMENTS

2009/0052169 A1*  2/2009  Kosters .................. F21V 11/02
                                                              362/224

FOREIGN PATENT DOCUMENTS

| DE | 69011854 T2 | 1/1995 | |
|---|---|---|---|
| DE | 102004058699 A1 * | 6/2006 | ............. B03C 3/011 |
| DE | 102021000458 A1 | 12/2021 | |
| DE | 102021115065 A1 | 12/2021 | |
| EP | 461310 A * | 12/1991 | ............... A61L 9/20 |

* cited by examiner

*Primary Examiner* — Andrew Smyth
(74) *Attorney, Agent, or Firm* — ArentFox Schiff LLP

(57) ABSTRACT

A lamellar arrangement for shielding radiation acting on a fluid which flows through an interior of a device, comprises two or more lamellae aligned substantially parallel to one another and respectively defining an intermediate space between them, wherein at least one subset of the lamellae is respectively subdivided into at least three lamella sections comprising a first lamella section, a second lamella section next to the first lamella section and a third lamella section next to the second lamella section. The first lamella section and the second lamella section in this case enclose a first angle between them, and the second lamella section and the third lamella section enclose a second angle between them. The first angle has a magnitude in a range of from 20° to 45° and the second angle has a magnitude in a range of from 20° to 45°.

15 Claims, 8 Drawing Sheets

_US 12,263,267 B2_

LAMELLAR ARRANGEMENT AND DEVICE FOR STERILIZING A FLUID BY MEANS OF UV RADIATION COMPRISING SUCH A LAMELLAR ARRANGEMENT

TECHNICAL FIELD

Aspects of the invention presented here relate to a lamellar arrangement for shielding radiation acting on a fluid which flows through an interior of a device. Further aspects relate to a device having the lamellar arrangement, which is configured for example to shield UV radiation for the sterilization of a fluid which flows through an interior of the device and through the lamellar arrangement.

PRIOR ART

It is known to provide ventilation and air recirculation systems, for example in buildings or air conditioning equipment, with UVC emitters in order to inactivate or kill germs or pathogens, for instance bacteria, bacterial spores, viruses or viroids, fungi, fungal spores or algae, etc., from indoor air. Often, for this purpose air is taken from the corresponding rooms, exposed to UVC radiation during processing, and finally returned to the corresponding room. A wavelength range corresponding to UVC radiation extends from 100 nm to 280 nm. For example, it is possible to use low pressure mercury vapor lamps that emit radiation or light with a wavelength of 254 nm, which is used for example for virus inactivation since in this case the viral nucleic acid is attacked. After a multiplicity of cycles, the bioburden in the relevant rooms may be reduced by more than 99% as a result of this treatment.

Particularly during the pandemic due to the coronavirus SARS-CoV-2, the need for corresponding UVC wall apparatuses or mobile UVC apparatuses has also increased greatly. These may sometimes also be operated in combination with photocatalysis.

In the field of the disinfection of liquids, furthermore, UVC reactors for the treatment of drinking water or for the sterilization of service water in dishwashers, etc. are also known, for example. In this case as well, the liquid is suitably exposed to UV radiation so that the germs therein are inactivated.

Moreover, apparatuses which use UVA and/or UVB radiation in addition to UVC radiation are also used. Furthermore, UV radiation is used in apparatuses in order to destroy biofilms accumulating at sensitive points therein.

When such apparatuses are used, however, questions of radiation protection in principle always have to be taken into account, since the UVC radiation released can also have a very harmful effect on eyes and skin, etc., of people in the event of exposure. In particular, special measures are therefore generally necessary in the aforementioned apparatuses and instruments, which ensure that the UVC radiation cannot emerge from the respective interior of the apparatuses.

To date, this has regularly been achieved by for example right-angled chicanes which achieve good shielding by their geometrical construction. These or similar measures, however, suffer from the disadvantage that during operation they lead to a comparatively large differential pressure in the fluid (gas such as for instance room air or waste air, or liquid such as for instance waste water or drinking water, etc.) and therefore ultimately to a lower volume throughput and a higher energy consumption.

DESCRIPTION OF ASPECTS OF THE INVENTION

The object of some of the aspects described below is to provide effective radiation protection, together with which a high volume throughput is obtained while having a comparatively lower power requirement for the fans or the pumps, so that the noise pollution can also be reduced.

The object is achieved by a lamellar arrangement for shielding radiation acting on a fluid which flows through an interior of a device. The fluid may, as described, be gases (such as for instance room air or waste air) or liquids (for instance waste water or drinking water etc.). The lamellar arrangement comprises two or more lamellae aligned substantially parallel to one another and respectively defining an intermediate space between them. The lamellar arrangement may be intended for positioning at the inlet and/or at the outlet of the apparatus and, for this purpose, be exposed to the radiation (for example UVC radiation) emitted by a radiation source into the interior through which flow takes place, in order to prevent radiation from emerging. According to individual aspects, one approach is to form the lamellae, and therefore the intermediate spaces or flow channels, so that they meander slightly but without causing sharply angled kink points which would lead to an increased differential pressure in the gas flowing through, or the corresponding liquid.

At least one subset of the lamellae is respectively subdivided for this purpose into at least three lamella sections comprising a first lamella section, a second lamella section next to the first lamella section and a third lamella section next to the second lamella section. There could also be further lamella sections to these. The first lamella section is respectively provided on the entry side (entry of the radiation), that is to say positioned closest to the radiation source and the interior. The second, third and further lamella sections may follow one after the other in the flow direction (outlet) or counter to the flow direction (inlet).

Not all lamellae of the lamellar arrangement need to be subdivided into the described lamella sections. Owing to the spatial shape of the lamellar arrangement overall, for example, lamellae placed at the edge may be shortened. Individual lamellae lying in between, which consist only of one or two lamella sections, may also be provided. Since, however, the lamellae should substantially match one another in order to allow a tight construction engaged on and in one another, it is recommendable for example to provide a majority of the lamellae of the arrangement in the manner described, in order to achieve the effects which said subset generate.

The first lamella section and the second lamella section may enclose a first angle between them, and the second lamella section and the third lamella section may enclose a second angle between them. The first angle in this case has a magnitude in a range of from 20° to 45° and the second angle likewise has a magnitude in a range of from 20° to 45°. In the general embodiment, the first and the second angle need not necessarily be equal. Studies have revealed that the angle range indicated for the lamella sections proves particularly effective in order to obtain only a very low differential pressure. The angle range indicated leads only to an at most very small increase in the flow resistance. At the same time, providing the lamellar arrangement per se proves particularly effective since the flow is opposed only by a low resistance despite the lamellae, while the lamellae either absorb the radiation which has penetrated into the intermediate spaces or flow channels because of the angled sections, or according to some embodiments partially reflect it into the interior. With a sufficiently small lamella spacing, the small angles are already enough to prevent direct emergence of radiation.

According to some exemplary embodiments, the respective sums of the lengths of the lamellae with the first and second orientation are approximately equal. The ratio of the sums should be from 0.5 to 2, preferably from 0.6 to 1.7, and particularly preferably from 0.7 to 1.4.

The lamella sections are preferably inherently flat or planar. Arching or curvatures are, however, in principle not excluded. It has, however, been found that flat sections having geometrically locally very limited kink points effectively reduce the transport through the intermediate spaces, or flow channels, of the radiation repeatedly reflected at the lamella sections.

The device for which the lamellar arrangement may be provided may, for example, be a device for shielding UV radiation for a device for sterilizing a fluid which flows through an interior of the device and through the lamellar arrangement. In such cases, the corresponding radiation sources may, inter alia, be UV LEDs or discharge lamps, etc., emitting radiation in the suitable wavelength range (UVA, UVB, UVC, etc.).

According to one refinement of the aspect described above, the magnitude of the first angle and the magnitude of the second angle are substantially equal. Furthermore, the angles extend in mutually opposite directions, so that the spatial orientations of the first lamella section and of the third lamella section are substantially parallel to one another. This corresponds to a particularly simple and compact construction.

According to another refinement of the lamellar arrangement, the first angle has a magnitude in a range of from 32° to 40° and the second angle, independently thereof, likewise has a magnitude in a range of from 32° to 40°. This narrowly defined angle range has been found to be particularly advantageous in terms of a balance between a rising differential pressure with increasing angles on the one hand, and increasing radiation transmission through the intermediate spaces with decreasing angles.

According to another refinement of the lamellar arrangement, the first lamella section and the second lamella section, and/or the second lamella section and the third lamella section (and possible junctions between further lamella sections), may be formed continuously. In particular, each lamella may in this case also be formed in one piece, for example produced from a bent metal sheet. The bending edges of all lamella sections may, for example, be oriented parallel to one another. The bending edges may, in the state installed in the housing of a UV disinfection device, be oriented substantially perpendicularly to the intended flow direction. A bending radius, which can scarcely be avoided for reasons of production technology, of the bending edges may be 2 mm or less. In one preferred embodiment, it may be 1 mm or less, more preferably even only 0.5 mm or less. As described above, the effect achieved by avoiding curved faces is that less of the repeatedly reflected radiation passes through the intermediate spaces, or flow channels, between the lamellae to the other side of the lamellar arrangement (for example to the outlet or inlet).

As an alternative, the first lamella section and the second lamella section, and/or the second lamella section and the third lamella section (and possible further junctions), may be formed separated from one another by a mutual spacing. Therefore, there is a gap between the lamella sections. The spacing may be 10 mm or less, preferably 5 mm or less.

Similarly as in the case above of the bending edge, the gaps may extend parallel to one another, for example, and have a constant mutual spacing, for example. The gaps between the lamella sections may, in the state installed in the housing of a UV disinfection device, be oriented substantially perpendicularly to the intended flow direction.

In principle, it is also possible for the first lamella section and the second lamella section, and/or the second lamella section and the third lamella section, to be formed separately from one another without a spacing. That is to say, they are in abutting contact with one another, but at least not formed continuously all along the kink line.

According to a further embodiment of the lamellar arrangement, at least one fourth lamella section, which is arranged next to the third lamella section and includes a third angle with the third lamella section, the magnitude of which lies in a range of from 20° to 45°, preferably in a range of from 32° to 40°, may respectively be provided in the lamellae at least of the subset. This aspect improves the meandering spatial shape of the lamellae and even more greatly reduces the radiation transmission while the differential pressure in the fluid flowing through remains substantially unchanged.

According to a further embodiment of the lamellar arrangement, a reflectance of one or both surfaces of all lamella sections is 15% or less, preferably 10% or less, more preferably 8% or less. Owing to such small values, the radiation entering the lamellar arrangement is effectively absorbed.

Furthermore, for this purpose the surface or the surfaces may be structured by a surface treatment. As a result of this, a full width at half maximum of the angles of the scattered radiation may be at least 10°, preferably at least 35° and particularly preferably at least 50°. The surface treatment may for example be carried out by sandblasting, etching, electrical discharge machining, pattern embossing and/or pattern milling, etc. Grinding, brushing, chemical matting, etc. may likewise be used. Owing to this measure, the radiation impinging on the surface is no longer only reflected directly (insofar as it is not absorbed), but is also partially back scattered to an effective extent. In particular, a structure that is known inter alia as a cat's eye, which sends the radiation back into the interior of the device, or of the reactor, in order to improve its efficiency may in this case be provided on or in the surface. Such an effect may be achieved by a right-angled strip relief (for example consisting of prismatic profiles). In a side view, as for example in FIG. 1, the strip relief would be represented as a right-angled zigzag line on the surfaces of the respective lamella section. Instead of special prismatic profiles, grooves or corrugations may also generally be provided.

According to a further embodiment of the lamellar arrangement, the one or both surfaces of the first lamella section may have a reflectance which is increased, unlike the further lamella sections. In other words, the reflectance is greater than a reflectance of one or both surfaces of the second and the third lamella section and, if present, of further lamella sections (which as described above is preferably less than 15%).

In particular, the reflectance of one or both surfaces of the first lamella section may be 30% or more, that is to say significantly increased. In addition, the surface(s) of the first lamella section may as described above be structured by a surface treatment, as a result of which a full width at half maximum of the angles of the scattered radiation is at least 10%, preferably at least 35% and particularly preferably at least 50%.

The latter two aspects taken together contribute to as much radiation as possible that has entered the intermediate space being sent back into the interior or reactor space by the lamella section lying closest to the interior, that is to say the first lamella section, and still being usable there as useful radiation. This leads to a higher energy efficiency of a device which uses the lamellar arrangement.

According to a further embodiment of the lamellar arrangement, a thickness of the lamella sections lies in a range of from 0.1 mm to 2 mm, preferably from 0.25 mm to 1 mm. The lamellar arrangement is therefore usable in a wide range of applications which, in particular, are suitable for the typical dimensions in UV sterilization apparatuses and equipment.

According to a further embodiment of the lamellar arrangement, at least two, preferably all lamellae of the subset have a substantially identical spatial shape to one another. This makes it possible, as described, to arrange the lamellae at a small spacing from one another and to achieve a compact design. In the lamellar arrangement, furthermore, those edges of the respective first lamella sections which are on the entry side in respect of the flow of the fluid define an entry plane, and those edges of the respective last lamella sections in the sequence which are on the exit side in respect of the flow of the fluid define an exit plane, the entry plane and the exit plane being parallel to one another. This is for the case of a lamellar arrangement to be positioned at the outlet, although similar considerations also apply for a lamellar arrangement at the inlet, where the first lamella section defined as being closest to the interior comprises the exit side edge.

In this embodiment, for an arrangement angle α, which specifies an inclination respectively of the entry plane and of the exit plane relative to a plane arranged perpendicularly in respect of the first lamella sections, in relation to an angle β, which corresponds to the first, second and optionally third angle (these are then identical to one another in this exemplary embodiment), the following relation is now satisfied:

$$\left|\frac{\cos(\beta-\alpha)}{\cos(\alpha)}-1\right|<0.2, \tag{1}$$

preferably:

$$\left|\frac{\cos(\beta-\alpha)}{\cos(\alpha)}-1\right|<0.15 \tag{2}$$

more preferably:

$$\left|\frac{\cos(\beta-\alpha)}{\cos(\alpha)}-1\right|<0.1 \tag{3}$$

In this way, a substantially constant intermediate space width may be obtained over the length of the respective lamella in the flow direction. In the ideal case, the value on the right-hand side of the relation is zero. The arrangement angle α is then exactly half as great as the angle β, between the lamella section orientations. By satisfying the relation above, the variance of the lamella spacings is restricted. Specifically, the variance has a detrimental effect on the resulting differential pressure of the fluid flowing through, since unavoidable constrictions at which the fluid can stagnate occur in the intermediate spaces.

According to a further embodiment of the lamellar arrangement, at least two, preferably all lamellae of the subset have a substantially identical design or spatial shape to one another, that is to say in this embodiment they are dimensioned substantially identically in terms of their bending angles and section lengths. In the lamellar arrangement, furthermore, those edges of the respective first lamella sections which are on the entry side in respect of the flow of the fluid define an entry plane, and those edges of the respective last lamella sections in the sequence which are on the exit side in respect of the flow of the fluid define an exit plane, the entry plane and the exit plane being parallel to one another. The comments made above for the corresponding case of a lamellar arrangement to be positioned at the inlet also apply here.

In this embodiment, for an arrangement angle α which specifies an inclination respectively of the entry plane and of the exit plane relative to a plane arranged perpendicularly in respect of the first lamella sections, in relation to an angle β which corresponds to the first, second and optionally third angle (also identical to one another here), and in relation to a distance d between mutually opposite first lamella sections, the following relation is now satisfied:

$$d<f\frac{l_1 l_2 \sin\beta}{l_1+l_2(\cos\beta+\sin\beta\tan\alpha)}, \tag{4}$$

where:
$l_1$: is the length of the first lamella section,
$l_2$: is the length of the second lamella section, and
f: is a factor for which f≤1, preferably f<0.5 with a full width at half maximum of the scattered radiation of less than 20°, and more preferably f<0.7 with a full width at half maximum of the scattered radiation of between 20° and 60°.

When this relation is satisfied, direct beam transmission of the UV radiation through the lamella intermediate spaces is prevented, or it is the case that no beam passes through the arrangement without impinging on at least two lamella sections. In the case of three lamella sections, correspondingly, the following additionally applies:

$$d<f\frac{l_2 l_3 \sin\beta}{l_2+l_3(\cos\beta+\sin\beta\tan\alpha)}, \tag{5}$$

and in the case of four lamella sections, additionally:

$$d<f\frac{l_3 l_4 \sin\beta}{l_3+l_4(\cos\beta+\sin\beta\tan\alpha)}, \tag{6}$$

where:
$l_3$: is the length of the third lamella section, and
$l_4$: is the length of the fourth lamella section.

With each further lamella section, the minimum number of necessary radiation impingement points (even in the case of ideal reflection) is then increased respectively by at least one.

According to a further embodiment of the lamellar arrangement, one or both surfaces of the lamella sections is/are coated with one of:
eloxal layers, in particular inorganic pigmentation; burnished, phosphatized or black-chromed metal coatings; ceramic coatings; metallizations on inorganic and organic substrates; metal oxide coatings, for example TiO₂; or photocatalytic coatings, in particular TiO₂, CeO or ZnO. By this measure, the reflectance of the lamella surfaces can be kept low. Preferably, the coatings are resistant to the impinging UV radiation (strength, durability). UV stabilized varnishes may also be included in these. Photocatalytic coatings are particularly expedient in UV applications in order to enhance the system efficiency, achieve the breakdown of odors and/or volatile organic compounds (VOCs), activate the relevant surface against microorganisms and at the same time assist self-cleaning effects.

The aforementioned objects are also achieved at least partially by a device for sterilizing a fluid flowing through the device by means of UV radiation. According to some aspects, the device may comprise:
 a housing having an inlet and an outlet for the fluid,
 a radiation source, which is configured to emit UV radiation into an interior in the housing through which fluid flows,
 the lamellar arrangement according to one of the aspects described above. The lamellar arrangement may in this case be positioned at the inlet or at the outlet as seen from the interior, in order to effectively prevent the UV radiation emerging from the housing, while the fluid can flow through the lamellar arrangement. The device may comprise a fan (gas) or a pump (liquid) or the like, in order to drive the flow of the fluid. With this use of the lamellar arrangement, the advantages described above are obtained to a significant extent.

The device may, in relation to gases to be sterilized, be UVC installations in ventilation equipment, UVC wall apparatuses for air sterilization, mobile UVC apparatuses, and in general UV apparatuses for air sterilization which emit radiation not only in the UVC range but as an alternative or in addition also in the UVA and UVB range, in order to exert their sterilizing effect. Apparatuses working in combination with photocatalysis may also be envisioned. In general, these devices are volumes (reaction chambers) through which gas flows, to the interior of which light propagation is intended to be limited in particular for reasons of radiation protection. In particular, the proposed lamellar arrangement may also provide protection against radioactive radiation or x-ray radiation.

The device may also, in relation to liquids to be sterilized, be water reactors with UVC radiation, in particular those for drinking water sterilization. In general, these are volumes (reaction chambers) through which liquid flows, to the interior of which light propagation is intended to be limited.

According to another embodiment of the device, the radiation source may comprise a plurality of individual radiation sources which are arranged in a row. The row of individual radiation sources may in this case be arranged along a straight connecting line, the straight connecting line extending in the interior substantially parallel to the first lamella sections of the lamellae and through the lamellar arrangement. In this way, not all individual radiation sources in the interior emit into the entry side of the lamellar arrangement, but only the individual radiation source lying closest, because it masks the rear individual radiation sources as seen from the lamellar arrangement.

As an alternative, a straight line mirrored at a reflective wall in the interior relative to the straight connecting line may extend substantially parallel to the first lamella sections of the lamellae and through the lamellar arrangement. This covers the case in which the closest individual radiation source emits into the intermediate space of the lamellar arrangement by means of reflection at the reflective wall because of the geometrical construction. So that the other individual radiation sources do not do the same, they are arranged in a row as above along the straight connecting line, which is obtained by mirroring, behind the closest individual radiation source.

According to another embodiment of this aspect, a blocker, which prevents the light beam from penetrating into the relevant intermediate space, may selectively be arranged between the radiation source and those first lamella sections which extend substantially parallel to the light beam incident directly from the radiation source or a light beam reflected directly by a reflective wall into the interior. In the case of neighboring lamellae, the angle of arrival may already be so great because of the positioning of the radiation source relative to the lamellar arrangement and the geometry that the beams no longer penetrate deeply into the intermediate space.

According to another embodiment of the device, a honeycomb structure is provided in the interior between the radiation source and the lamellar arrangement, the honeycomb structure forming a body having a multiplicity of tubular cells which are mutually parallel in a transmission direction. The honeycomb structure is in this case aligned in respect of the radiation source and the lamellar arrangement in such a way that a plane orthogonal to the transmission direction of the honeycomb structure includes an arrangement angle γ with a plane which is positioned perpendicularly to the first lamella sections, the arrangement angle γ having a magnitude in a range of from 20° to 45°. The functional principle and the advantages are similar to those described above in respect of the lamellar arrangement itself. For a UV application, for example, a functional coating of TiO₂ may be preferred.

Further advantages, features and details of the invention may be found from the claims, the following description of preferred embodiments and with the aid of the drawings. In the figures, references which are the same denote features and functions which are the same.

BRIEF DESCRIPTION OF THE DRAWING(S)

In the following description of preferred exemplary embodiments, it should be borne in mind that the present disclosure of the various aspects is not restricted to the details of the construction and the arrangement of the component parts as are presented in the following description and in the figures. The exemplary embodiments may in practice be implemented or carried out in a variety of ways. It should furthermore be borne in mind that the expressions and terminology used here are used only for the purpose of the specific description and they should not be interpreted restrictively as such by the person skilled in the art.

Figure 1:
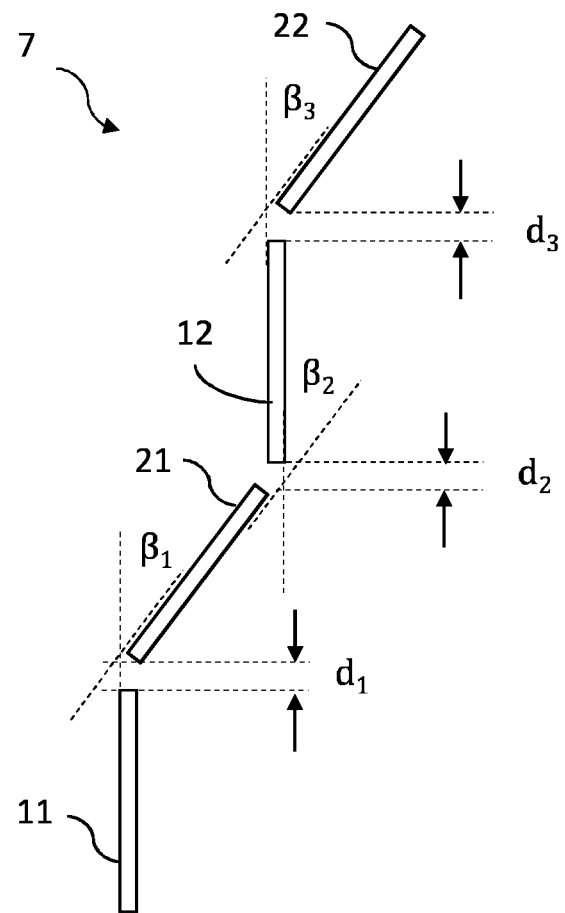
FIG. 1 shows a schematic representation of an individual lamella, having four mutually separated lamella sections, of a lamellar arrangement according to a first exemplary embodiment in an in-plane view (the lamella extends perpendicularly to the plane of the drawing)

An individual lamella is shown in a schematic representation in FIG. 1. In particular, an individual lamella 7, having four mutually separated lamella sections 11, 12, 21 and 22, of a lamellar arrangement according to a first exemplary embodiment is shown therein in an in-plane view. The lamella 7 in this case extends perpendicularly to the plane of the drawing.

The four lamella sections 11, 12, 21 and 22 are essentially plate-shaped and respectively extend in a plane. In the particular exemplary embodiment, they have the same size as one another, that is to say the same depth into the plane of the drawing and the same length in the plane of the drawing. A thickness is, for example, between 0.25 mm and 1 mm.

The material of the lamella 7, or of the lamella sections 11, 12, 21 and 22 which make up the lamella, may be any desired material, albeit one which is preferably resistant to the radiation used (in particular UVC radiation) in order to avoid detrimental modification of the optical and mechanical properties over the irradiation time and lifetime. The formation of detrimental material fragments (in particular volatile organic compounds, VOCs), which could occur as a result of material destruction, should also be avoided. Correspondingly, metals such as aluminum (UV radiation, beta radiation), steels (for example stainless steel), lead (for very short-wave radiation) or other metals/metal alloys (copper, etc.) may preferably be used. If the intention is to shield against a radiation instead of UV radiation, paper may also be envisioned. Ceramic materials or special plastics, for instance polymers with comparatively high bond energies (for UV), for example fluorinated plastics or silicones, or polymers which are UV stabilized by adding inhibitors or appropriate color pigments, or which are protected from the radiation by suitable metal coatings, may also be suitable.

Furthermore preferred are materials which (insofar as they are not correspondingly coated) restrict radiation propagation in the intermediate space between the lamellae 7 by significant absorption and reduced reflectivity.

In the present exemplary embodiment, the lamella sections 11, 12, 21 and 22 are, for example, ones made of aluminum. The sections may also consist of different materials to one another The lamella sections 11, 12, 21 and 22 may also be coated. Possible coatings are mentioned above. In the present exemplary embodiment, it is an eloxal layer (eloxal: electrolytic oxidation of aluminum), which has particularly outstanding properties in terms of both low reflectance and highly diffuse scattering in respect of the remaining radiation still emitted, particularly if the surface of the material is roughened or correspondingly treated before the anodic oxidation. In particular, an eloxal layer comprising metal oxides as inorganic pigmentation may in this case be envisioned.

In the case of installation in a device for sterilizing a fluid, the first lamella section 11 is placed as close as possible to the corresponding radiation source. As a radiation entry lamella section, it is provided (or its two surfaces are provided) in the exemplary embodiment with a comparatively high reflectance of more than 30%. The reflectance of the surfaces of the other three "rear" lamella sections 12, 21 and 22 is on the other hand only 8% or less in the particular exemplary embodiment. At the same time, the surfaces of the first lamella section 11 are finished so that they have a very high full width at half maximum for the angles of the scattered radiation, for example an approximately Lambertian radiation characteristic. The advantage obtained by this measure is due to the fact that the back-scattered radiation is scattered back into the region of action of the radiation before the lamellar arrangement (that is to say into the interior of the device) and the efficiency of the desired effect, for example the inactivation of microorganisms by UVC radiation, can be further enhanced.

Returning to FIG. 1, the second lamella section 21 is arranged inclined relative to the first lamella section 11, that is to say they include a first angle $\beta_1$. The flow direction of the fluid is within the plane of the drawing in FIG. 1, and is for example directed upward past the lamella 7 here. Because of the inclination, the flow is deflected toward the right in the plane of the drawing. The first angle $\beta_1$ is 35° in the particular exemplary embodiment.

A second angle $\beta_2$ is likewise included between the second lamella section 21 and the third lamella section 12, although the inclination of the third lamella section 12 relative to the second lamella section 21 is spatially opposite to the inclination of the second lamella section 21 relative to the first lamella section 11. Because of the inclination, the flow is deflected toward the left in the plane of the drawing. The second angle $\beta_2$ is also 35° in the particular exemplary embodiment, that is to say $\beta_1 = \beta_2$.

A third angle $\beta_3$ is also included between the third lamella section 12 and the fourth lamella section 22, although the inclination of the fourth lamella section 22 relative to the third lamella section 12 is in turn spatially opposite to the inclination of the third lamella section 12 relative to the second lamella section 21. Because of the inclination, the flow is again deflected toward the right in the plane of the drawing. The second angle $\beta_3$ is also 35° in the particular exemplary embodiment, that is to say $\beta_1 = \beta_2 = \beta_3$. Deviations in the range of <2°, preferably <1° are however to be taken into account, in particular as a result of production.

By this construction of the lamella 7, the first lamella section 11 and the third lamella section 12 are arranged spatially parallel and offset with respect to one another. Likewise, the second lamella section 12 and the fourth lamella section 22 are arranged spatially parallel and offset with respect to one another.

As may be seen in the exemplary embodiment shown in FIG. 1, the lamella sections are arranged in a row with a comparatively acute angle (35°) with respect to one another. They respectively have edges on the entry side and edges on the exit side (for radiation entry and exit, the radiation in FIG. 1 being considered to come vertically from below). The exit side edge of the first lamella section 11 has a spacing $d_1$ from the entry side edge of the second lamella section 21. The exit side edge of the second lamella section 21 has a spacing $d_2$ from the entry side edge of the third lamella section 12. The exit side edge of the third lamella section 12 has a spacing $d_3$ from the entry side edge of the fourth lamella section 22. The spacings $d_1$, $d_2$ and $d_3$ are identical here, and in the particular exemplary embodiment are less than 5 mm (essentially for reasons of space). As may be seen in FIG. 2 with the aid of the dashed lines, the lamella sections 11, 12, 21 and 22 next to one another are mutually arranged so that the entry side edge of the subsequent lamella section and the projection of the neighboring edges in the flow direction 8 of the fluid respectively lie above one another (see FIG. 2). The differential pressure resulting from the air flow between the input and the output is therefore kept low.

Figure 2:
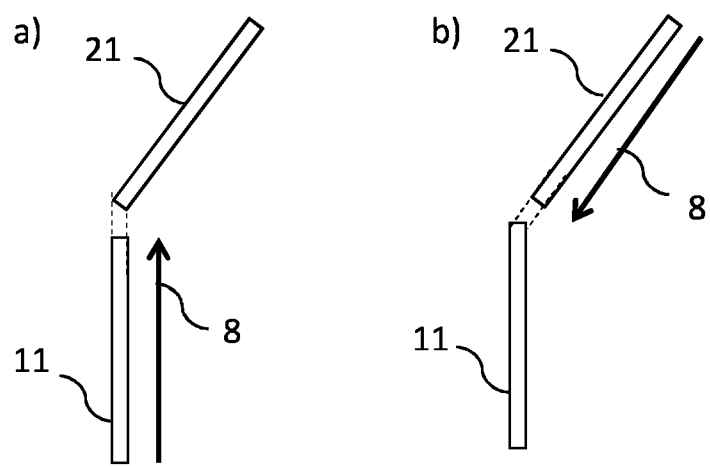
FIG. 2 shows a relative arrangement of the ends of mutually separated lamellae in FIG. 1.

The direction indications refer to a lamellar arrangement at the outlet of a device, see part a) in FIG. 2. Part b) shows the reverse case of the lamellar arrangement at the inlet of the device (the first lamella section 11 is respectively defined here as being directed toward the radiation source).

Figure 3:
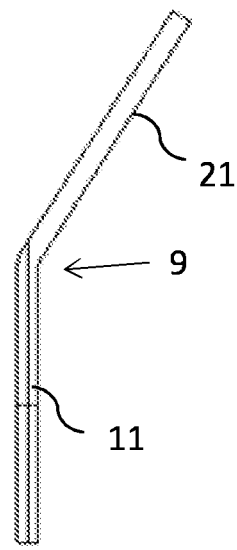
FIG. 3 shows an exemplary embodiment of mutually connected lamellae bent through an angle over a bending edge.

FIG. 3 shows a variant of the exemplary embodiment of FIG. 2. Here, the first lamella section 11 and the second lamella section 21 are formed continuously over a bending edge 9. The angle $\beta_1$ is in this case purely by way of example 30°. The further lamella sections 12 and 22 as well as the corresponding angles $\beta_2$ and $\beta_3$ are configured similarly. The bending radius of the bending edge is 0.5 mm or less in the particular exemplary embodiment. This avoids relevant scattering of radiation by the rounded subsurface at the bending edge entering the intermediate space of subsequent lamella sections.

Figure 4:
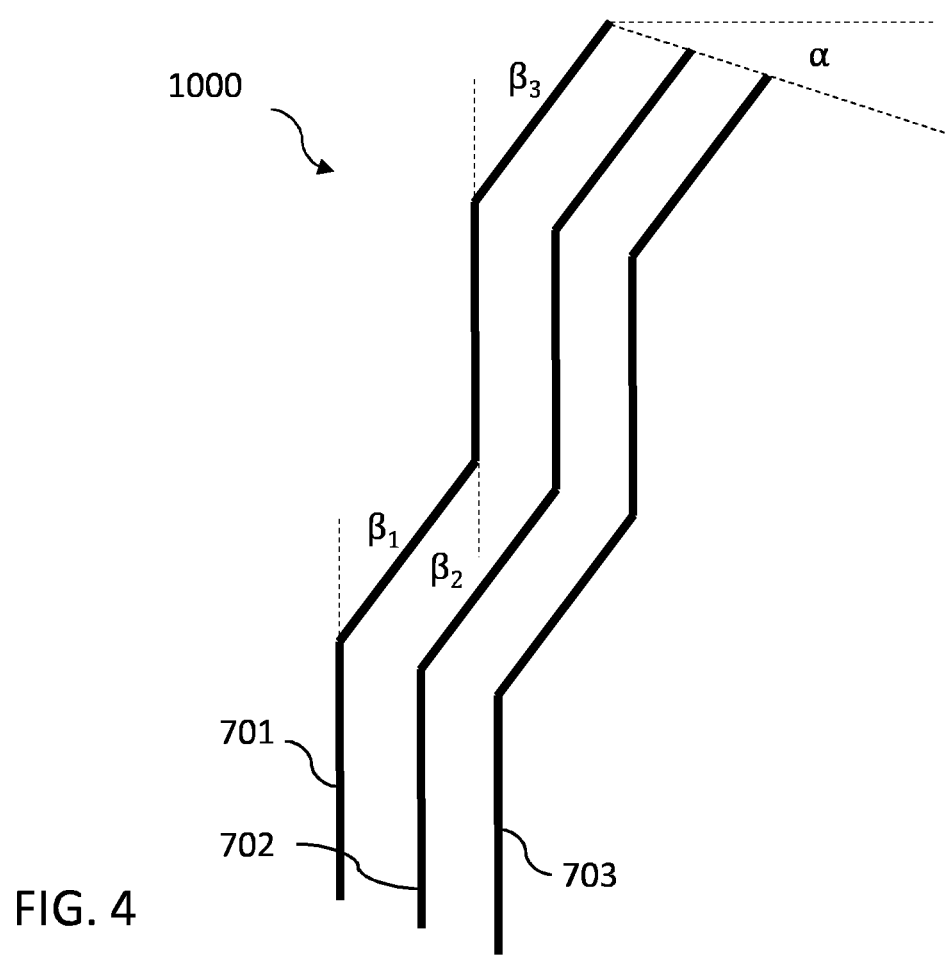
FIG. 4 shows an exemplary embodiment of a lamellar arrangement having lamellae connected as in FIG. 3.

FIG. 4 shows a schematic overview of a lamellar arrangement 1000 according to a second exemplary embodiment, which comprises lamellae 701, 702 and 703. The lamellae 701, 702 and 703 may correspond to the lamellae 7 shown in FIGS. 1 to 3. The lamellar arrangement comprises at least two (depicted: three) lamellae 701, 702 and 703 which have the same construction within the scope of producibility and are assembled by holders (not shown). Exit side edges of the respective last (fourth) lamella sections 22 in the assembled state span a plane which is inclined by an arrangement angle $\alpha$ relative to a normal plane, which is perpendicular to the plane spanned by the entry side first lamella sections 11. The arrangement angle $\alpha$ of the assembled lamellae 701, 702 and 703, etc. is ideally half as great as the angles $\beta_1$, $\beta_2$ and $\beta_3$ between the relevant lamella orientations. An estimate of deviations from this ideal case that are still acceptable is given above in the general part of the description (see conditions (1), (2) and (3) for the relationships between the arrangement angle $\alpha$ and the angle $\beta=\beta_1=\beta_2=\beta_3$).

Figure 5:
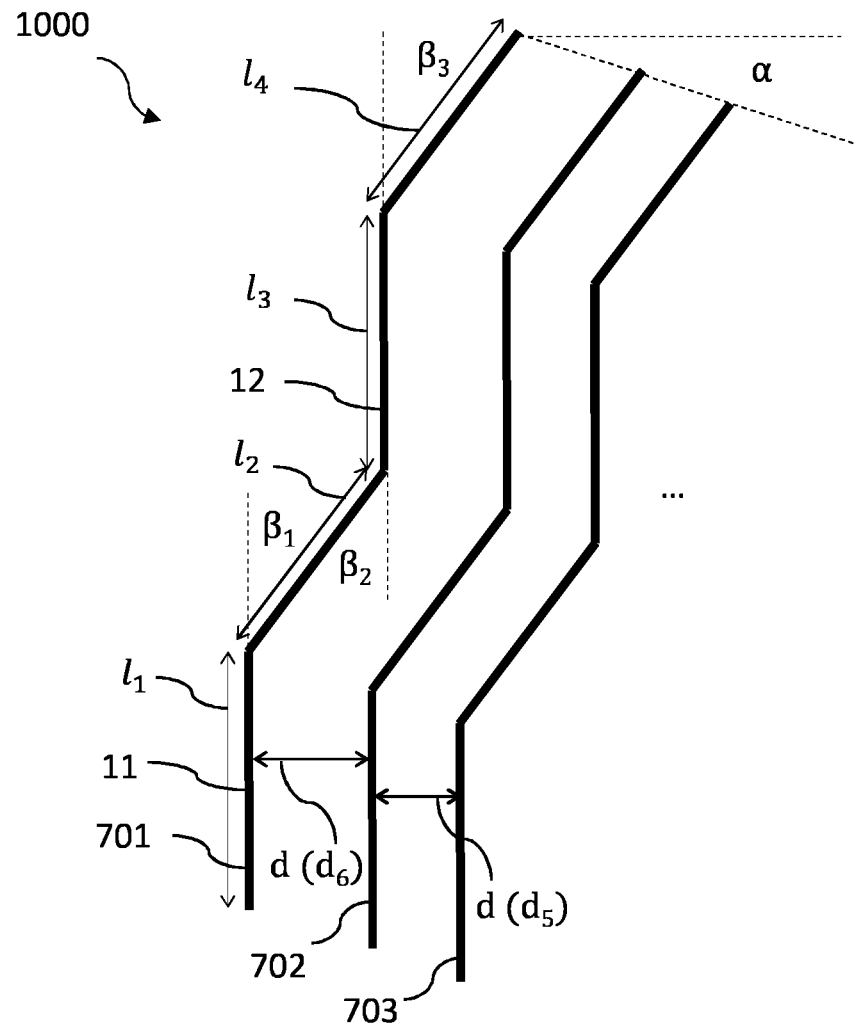
FIG. 5 shows an illustration of the calculation of a spacing required between lamellae of FIG. 4 for the lamellar arrangement.

FIG. 5 illustrates the calculation of the required spacing d between lamellae 701, 702 and 703 of the lamellar arrangement 1000 shown in FIG. 4, by which direct radiation transmission is prevented, and by taking into account factors $f \leq 1$ in correspondingly set up conditions (4), (5) and (6)—see above in the general part of the description—the minimization of radiation travelling indirectly in the exit direction by reflections or by scattering is also taken into account. For example, two different spacings d are indicated in FIG. 5, one larger $d_6$ and one smaller $d_5$. The spacing $d_6$ is likely to be too large when considered purely geometrically, while the spacing $d_5$ defines an upper limit for the spacing selection according to conditions (4), (5) and (6). In terms of the designations of the lengths of the lamella sections, see the explanation above.

Figure 6:
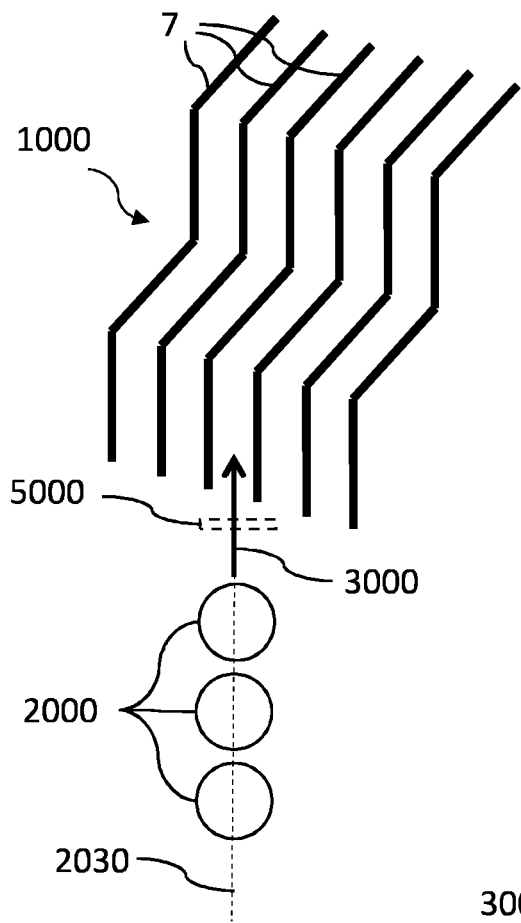
FIG. 6 shows a very schematic representation of a first exemplary embodiment of a device for shielding radiation acting on a fluid which flows through an interior of the device.

FIG. 6 shows, with the aid of a very schematically represented exemplary embodiment, a device for shielding radiation acting on a fluid which flows through an interior of a device, the way in which the lamellar arrangement 1000 according to the exemplary embodiments above is advantageously aligned with a radiation source 2000 composed of a plurality of individual sources. A housing having an inlet and an outlet for the fluid, and optionally a pump or a fan, are not also indicated for the sake of simplicity. The elements indicated in FIG. 6 are located in the interior of a housing. In this case, the individual sources are arranged in such a way that they emit as little radiation 3000 as possible in the direction of the lamellar arrangement 1000. In particular, that part of the radiation 3000 which impinges on the lamella section 11 defining the entry of the lamellar arrangement 1000 at a comparatively small angle thereto should be kept small. In the exemplary embodiment of FIG. 6, this is achieved by arranging the individual sources in a row. This row is aligned along a straight connecting line 2030. Furthermore, this straight connecting line 2030 is arranged parallel to the lamella section 11 defining the entry of the lamellar arrangement 1000. That fraction of the radiation 3000 which then penetrates along the straight connecting line 2030 (that is to say parallel thereto) into the intermediate space between the lamella sections 11 of neighboring lamellae 7 is attenuated by the individual source at the front masking the ones behind. This leads to a further reduction of the emergence of radiation.

Furthermore, a blocker 5000, for example a metal sheet, which prevents the light beam from penetrating into the relevant intermediate space which extends straight, exactly parallel to the direction of the radiation 3000, may selectively be arranged in the interior before the lamellar arrangement 1000, or the entry side of the latter, since the depth of directly penetrating radiation would possibly be particularly large here. The blocker may advantageously also be configured to be reflective.

Figure 7:
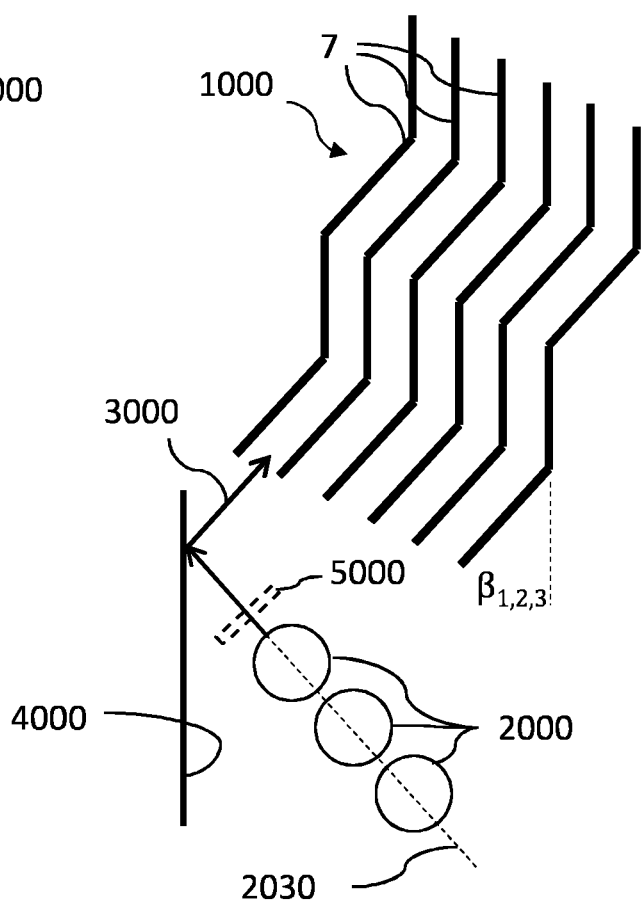
FIG. 7 shows a very schematic representation of a second exemplary embodiment, alternative to FIG. 6, of a device for shielding radiation acting on a fluid which flows through an interior of the device.

FIG. 7 shows an exemplary embodiment, which is an alternative or may be combined with FIG. 6, of a device for shielding radiation acting on a fluid which flows through an interior of the device. The representation is shown similarly as in FIG. 6 (no housing, no fan or pump, etc.). In this exemplary embodiment, a reflective wall 4000 extends in the interior, or is for example an inner wall of the housing, which defines the interior. Here as well, the individual sources of the radiation source are arranged in a row along the straight connecting line. That radiation fraction which is aligned parallel to the lamella section 11 defining the entry of the lamellar arrangement 1000 after reflection at the wall 4000 describes the direction of the straight connecting line 2030 and therefore the spatial alignment of the row of individual sources of the radiation source 2000. The same advantages as described with reference to FIG. 6 are achieved. Furthermore, a blocker 5000 may also be used here as in FIG. 6.

Figure 8:
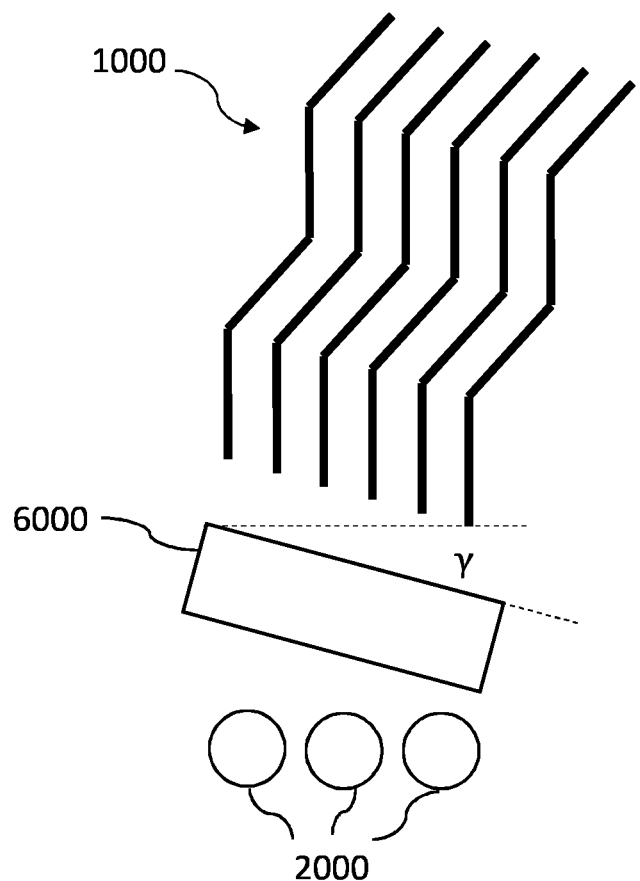
FIG. 8 shows a further third exemplary embodiment of a device for shielding radiation acting on a fluid which flows through an interior of the device, which comprises a honeycomb structure that prevents direct radiation entry along the lamella alignment.
Figure 9:
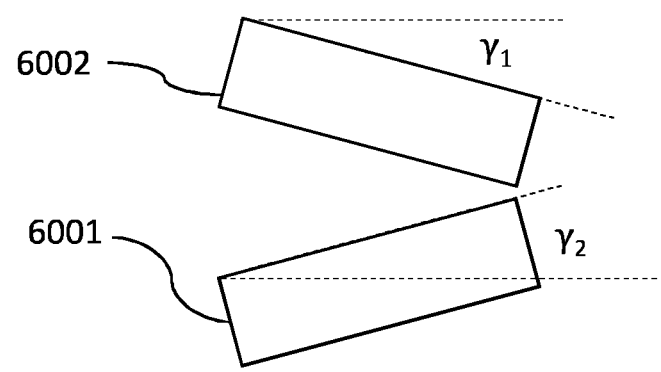
FIG. 9 shows alternative alignments of the honeycomb structure relative to the lamellar arrangement according to the exemplary embodiment in FIG. 8.
Figure 10:
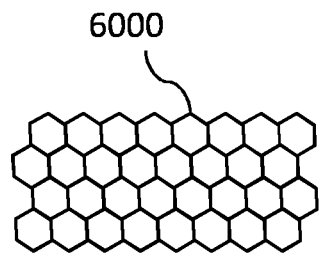
FIG. 10 shows the construction of a honeycomb structure of FIGS. 8 and 9 in a front view with individual cell openings.

FIGS. 8 to 10 show a further exemplary embodiment of a device for shielding radiation acting on a fluid which flows through an interior of the device. In order to prevent radiation entry here parallel to the lamella sections 11 which define the entry into the lamellar arrangement 1000, instead of or in addition to arranging the individual sources of the radiation source 2000 in a row, a honeycomb structure 6000 is used, the basic construction of which may be seen in the front view in FIG. 10. By a structure, which is hexagonal in cross section, of tubular cells of the honeycomb structure 6000, a high packing density is achieved. The tubular cells are coated with a reflection layer, preferably of $TiO_2$, and extend parallel to one another, while defining a transmission direction for the radiation.

The end face which is perpendicular to the transmission direction (and which thus represents the entry and exit face of the cells) of the honeycomb structure 6000 is aligned in respect of the radiation source 2000 and the lamellar arrangement 1000. The plane which is formed by the end face, and which is orthogonal to the transmission direction, in this case includes an arrangement angle $\gamma$ with a plane, which is positioned perpendicularly to the first lamella sections 11, which define the entry into the lamellar arrangement 1000. In other words, the transmission direction of the cells is inclined by the arrangement angle $\gamma$ relative to the alignment of the first lamella sections 11. The arrangement angle $\gamma$ has a magnitude in a range of from 20° to 45°, and is for example about 20°. It is shown in FIG. 9 for the honeycomb structures 6001 and 6002 that the arrangement angle $\gamma$ is not defined in the azimuthal direction. In respect of the direction of the angles $\beta_1$, $\beta_2$, $\beta_3$, the arrangement angle $\gamma$ may be selected freely, as is represented with the aid of $\gamma_1$ and $\gamma_2$.

The end faces indicated in FIGS. 8-10 need not necessarily be orthogonal to the transmission direction. The honeycomb structures may also be intersected at an inclined angle (different than 90°). This may advantageously lead to the possibility of placing a plurality of honeycomb structures next to one another without gaps, or with a small spacing which is constant over the end faces.

Figure 11:
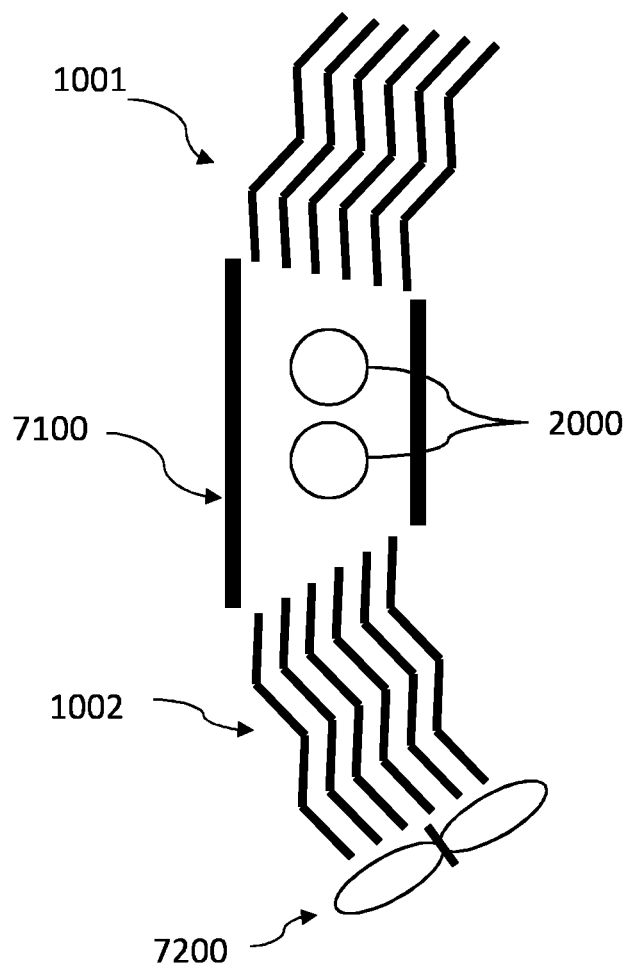
FIG. 11 shows a fourth exemplary embodiment of a device for shielding radiation acting on a fluid which flows through an interior of the device, the device being configured here as a UV air sterilizer.

FIG. 11 shows a further exemplary embodiment of a device for shielding radiation acting on a fluid which flows through an interior of the device. This figure may also serve as an example of a more general construction for a UV air sterilizer, which may adopt the particular features of the devices according to FIGS. 6, 7 and 8. FIG. 11 shows the housing, or in particular (the reactor) inner housing 7100, which defines the interior through which the fluid flows. The interior also contains the radiation source 2000, represented here schematically by two individual sources. Lamellar arrangements 1001 and 1002 are furthermore provided at the inlet and outlet for the fluid. The lamellar arrangements 1001 and 1002 shield the environment, or the exterior of the housing or of the device, from the radiation. The reactor inner housing 7100 is internally mirrored in order to allow efficient use of the radiation of the radiation source 2000, in the particular exemplary embodiment UVC lamps. The fan arrangement 7200 causes forced convection through the reactor, or the device. Because of the oblique setting of the fan arrangement 7200 relative to the housing axis, it is possible to use a larger fan diameter so as to obtain better pressure stability. Expedient air throughputs lie in the range of a volume flow rate of 200-1000 m³/h for a compact apparatus, which can be used for example in classrooms and conference rooms. Naturally, lower or higher throughput rates may be envisioned depending on the apparatus size. In this figure—as well as in other figures—optional components such as filters, parts of the apparatus for guiding the air, for operation and for the optics are not represented for the sake of simplicity.

Figure 12:
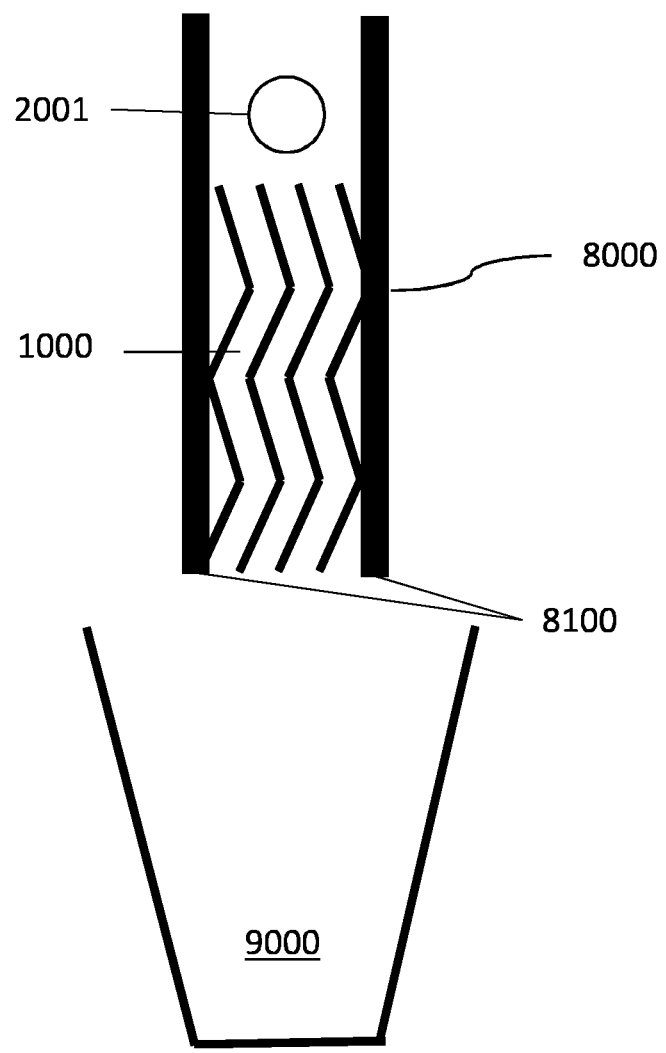
FIG. 12 shows a lamellar arrangement which may be used with a low differential pressure at the outlet of a water dispenser, implemented as a fifth exemplary embodiment of a device for shielding radiation acting on a fluid which flows through an interior of the device.

FIG. 12 shows a lamellar arrangement 1000 which can be used with a low differential pressure at the outlet 8100 of the water tube 8000 of a water dispenser. A low-power pump (not represented) may therefore be used, or merely the hydrostatic pressure may be employed without a pump. The reference 9000 denotes a water cup.

It should be noted that the lamellar arrangements described in detail here may expediently be used in all UVC transparent media: gases, for example air, or liquids, for example drinking water.

Figure 13:
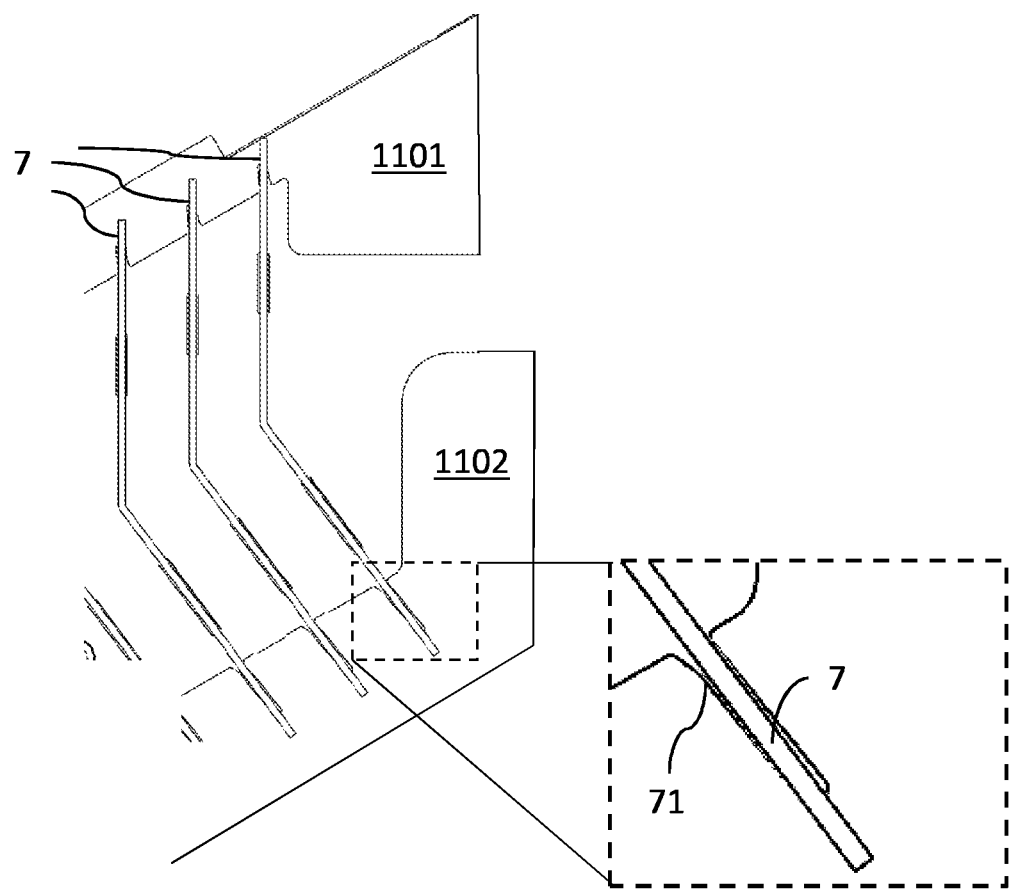
FIG. 13 shows an advantageous solution for the mechanical holding of the lamellae of a lamellar arrangement according to one of the exemplary embodiments of FIGS. 1 to 12.

FIG. 13 illustrates an advantageous solution for the mechanical holding of the lamellae 7 of a lamellar arrangement 1000. The lamellae 7 are assembled with a plurality of combs 1101, 1102 to form a lamellar assembly for mounting. In this case, for example during final mounting, the lamellae 7 are rotated relative to the combs by an angle of 2°-3° in the slots 71 of the combs 1101, 1102. The play between the lamellae 7 and the combs 1101, 1102 is therefore eliminated and the lamellae 7 do not rattle and do not cause annoying noise, but instead are fixed flexibly with a low mechanical tension.

LIST OF REFERENCES

7 lamella
8 flow direction
9 bending point
11 first lamella section
21 second lamella section
12 third lamella section
22 fourth lamella section
71 slots (in the combs)
701 lamella
702 lamella
703 lamella
1000 lamellar arrangement
1001 lamellar arrangement
1002 lamellar arrangement
1101 comb (mechanical holder for lamellae)
1102 comb (mechanical holder for lamellae)
2000 radiation source (optionally having a plurality of individual sources)
2001 radiation source (at the outlet of a water dispenser)
2030 straight connecting line (for arrangement of the individual sources in a row)
3000 radiation
4000 reflective wall (optionally of the inner housing)
5000 blocker (for example aluminum sheet)
6000 honeycomb structure
6001 honeycomb structure
6002 honeycomb structure
7100 housing (inner housing defining interior)
8000 water tube of a water dispenser
8100 outlet (or opening thereof)

The invention claimed is:

1. A lamellar arrangement for shielding radiation acting on a fluid which flows through an interior of a device, comprising:

two or more lamellae aligned substantially parallel to one another and respectively defining an intermediate space between them;

wherein at least one subset of the lamellae is respectively subdivided into at least three lamella sections comprising a first lamella section, a second lamella section next to the first lamella section and a third lamella section next to the second lamella section;
wherein the first lamella section and the second lamella section enclose a first angle between them, and the second lamella section and the third lamella section enclose a second angle between them;
wherein the first angle has a magnitude in a range of from 20° to 45° and the second angle has a magnitude in a range of from 20° to 45°;
wherein a reflectance of one or both surfaces of the first lamella section is greater than a reflectance of one or both surfaces of the second and third lamella sections and, if present, of further lamella sections
wherein the reflectance of one or both surfaces of the first lamella section is 30% or more, and the one or both surface of the first lamella section are structured by a surface treatment, as a result of which a full width at half maximum of angles of a scattered radiation is at least 10°, or at least 35° or at least 50°.

2. The lamellar arrangement as claimed in claim 1, wherein
the magnitude of the first angle and the magnitude of the second angle are substantially equal and a direction of the angles is mutually opposite, so that a spatial orientations of the first lamella section and of the third lamella section are substantially parallel to one another.

3. The lamellar arrangement as claimed in claim 1, wherein
wherein the first angle has a magnitude in a range of from 32° to 40° and the second angle has a magnitude in a range of from 32° to 40°.

4. The lamellar arrangement as claimed in claim 1, wherein
the first lamella section and the second lamella section, and/or the second lamella section and the third lamella section, are formed continuously, a bending radius being 2 mm or less, or 1 mm or less, or 0.5 mm or less; or
the first lamella section and the second lamella section, and/or the second lamella section and the third lamella section, are formed separated from one another by a mutual spacing, the spacing being 10 mm or less, or 5 mm or less; or
the first lamella section and the second lamella section, and/or the second lamella section and the third lamella section, are formed separately from one another without a spacing.

5. The lamellar arrangement as claimed in claim 1, wherein
at least one fourth lamella section, which is arranged next to the third lamella section and includes a third angle with the third lamella section, the magnitude of which lies in a range of from 20° to 45°, or in a range of from 32° to 40°, is respectively provided in the lamellae at least of the subset.

6. The lamellar arrangement as claimed in claim 1, wherein
a reflectance of one or both surfaces of all lamella sections is 15% or less, or 10% or less, or 8% or less.

7. The lamellar arrangement as claimed in claim 6, wherein
the one or both surfaces are structured by a surface treatment, as a result of which a full width at half maximum of angles of a scattered radiation is at least 10°, or at least 35° or at least 50°.

8. The lamellar arrangement as claimed in claim 1, wherein a thickness of the lamella sections lies in a range of from 0.1 mm to 2 mm, or from 0.25 mm to 1 mm.

9. The lamellar arrangement as claimed in claim 5, wherein
at least two, or all, lamellae of the subset have a substantially identical spatial shape to one another,
those edges of the respective first lamella sections which are on an entry side in respect of the flow of the fluid define an entry plane, and those edges of respective last lamella sections in a sequence which are on an exit side in respect of the flow of the fluid define an exit plane, the entry plane and the exit plane being parallel to one another, and
an arrangement angle ($\alpha$), which specifies an inclination respectively of the entry plane and of the exit plane relative to a plane arranged perpendicularly in respect of the first lamella sections, in relation to an angle ($\beta$), which corresponds to the first angle, the second angle, and optionally the third angle, that satisfies the following relation:

$$\left|\frac{\cos(\beta - \alpha)}{\cos(\alpha)} - 1\right| < 0.2,$$

$$\left|\frac{\cos(\beta - \alpha)}{\cos(\alpha)} - 1\right| < 0.15$$

$$\left|\frac{\cos(\beta - \alpha)}{\cos(\alpha)} - 1\right| < 0.1,$$

in order to obtain a substantially constant intermediate space width over a length of the respective lamella in a flow direction.

10. The lamellar arrangement as claimed in claim 5, wherein
at least two, or all, lamellae of the subset have a substantially identical spatial shape to one another,
those edges of the respective first lamella sections which are on an entry side in respect of the flow of the fluid define an entry plane, and those edges of respective last lamella sections in a sequence which are on an exit side in respect of the flow of the fluid define an exit plane, the entry plane and the exit plane being parallel to one another, and
an arrangement angle ($\alpha$), which specifies an inclination respectively of the entry plane and of the exit plane relative to a plane arranged perpendicularly in respect of the first lamella sections, in relation to an angle ($\beta$) which corresponds to the first angle, the second angle, and optionally the third angle, and in relation to a distance (d) between mutually opposite first lamella sections, that satisfies the following relation:

$$d < f \frac{l_1 l_2 \sin\beta}{l_1 + l_2(\cos\beta + \sin\beta\tan\alpha)},$$

where:
$l_1$: is a first length of the first lamella section,
$l_2$: is a second length of the second lamella section, and
f: is a factor for which f≤1, or f<0.5 with a full width at half maximum of the scattered radiation of less than 20°, or f<0.7 with a full width at half maximum of a scattered radiation of between 20° and 60°,
in order to avoid or at least reduce transmission of the radiation through the lamellae.

11. The lamellar arrangement as claimed in claim 1, wherein one or both surfaces of the lamella sections is/are coated with one of:

eloxal layers or inorganic pigmentation; burnished metal coatings, phosphatized metal coatings, or black-chromed metal coatings; ceramic coatings;

metallizations on inorganic substrates and organic substrates; metal oxide coatings; or photocatalytic coatings $TiO_2$, CeO, or ZnO.

12. A device for sterilizing a fluid flowing through the device by means of UV radiation, comprising:

a housing having an inlet and an outlet for the fluid, a radiation source, which is configured to emit UV radiation into an interior in the housing through which fluid flows, the lamellar arrangement as claimed in claim 1, the lamellar arrangement being positioned at the inlet and/or at the outlet as seen from the interior, in order to prevent the UV radiation emerging from the housing, while the fluid can flow through the lamellar arrangement.

13. The device as claimed in claim 12, wherein the radiation source comprises a plurality of individual sources which are arranged in a row, the row of individual sources being arranged along a straight connecting line, wherein the straight connecting line extends in the interior substantially parallel to the first lamella sections of the lamellae and through the lamellar arrangement, or wherein a straight line mirrored at a reflective wall in an interior relative to the straight connecting line extends substantially parallel to the first lamella sections of the lamellae and through the lamellar arrangement.

14. The device as claimed in claim 12, wherein a blocker, which prevents a light beam from penetrating into a relevant intermediate space, is selectively arranged between the radiation source and those first lamella sections which extend substantially parallel to the light beam incident directly from the radiation source or a light beam reflected directly by a reflective wall into the interior.

15. The device as claimed in claim 12, wherein a honeycomb structure is provided in the interior between the radiation source and the lamellar arrangement, the honeycomb structure forming a body having a multiplicity of tubular cells which are mutually parallel in a transmission direction, wherein the honeycomb structure is aligned in respect of the radiation source and the lamellar arrangement in such a way that a plane orthogonal to the transmission direction of the honeycomb structure includes an arrangement angle with a plane which is positioned perpendicularly to the first lamella sections, wherein the arrangement angle has a magnitude in a range of from 20° to 45°.

* * * * *